United States Patent
Lazarev et al.

[11] Patent Number: 5,986,271
[45] Date of Patent: Nov. 16, 1999

[54] FLUORESCENCE IMAGING SYSTEM

[76] Inventors: Victor Lazarev, 6 Baron Park La., Apt. 14, Burlington, Mass. 01803; Yuri E. Kazakevich, 26 Farrwood Dr., Andover, Mass. 01810; Robert A. Roth, 29 Hyslop Rd., Brookline, Mass. 02146; Jim Hang, 60 S. Bedford St., Woburn, Mass. 01801

[21] Appl. No.: 08/888,067

[22] Filed: Jul. 3, 1997

[51] Int. Cl.⁶ .................................................. G01N 21/64
[52] U.S. Cl. ........................ 250/458.1; 250/461.1; 250/461.2
[58] Field of Search ............... 250/461.2, 461.1, 250/458.1

[56] References Cited

U.S. PATENT DOCUMENTS

| | | |
|---|---|---|
| 4,556,057 | 12/1985 | Hiruma et al. . |
| 4,786,813 | 11/1988 | Svanberg et al. . |
| 5,097,135 | 3/1992 | Makino et al. .................. 250/461.1 |
| 5,115,137 | 5/1992 | Andersson-Engels et al. . |
| 5,408,996 | 4/1995 | Salb . |
| 5,418,371 | 5/1995 | Aslund et al. . |
| 5,507,287 | 4/1996 | Palcic et al. . |

FOREIGN PATENT DOCUMENTS

| | | |
|---|---|---|
| 0 405 480 A2 | 1/1991 | European Pat. Off. ............ 250/461.2 |
| 60-61648 | 4/1985 | Japan . |
| 2-183147 | 7/1990 | Japan . |
| 2-310448 | 12/1990 | Japan .................................. 250/461.2 |
| 2 254 417 | 10/1992 | United Kingdom . |

*Primary Examiner*—Constantine Hannaher
*Attorney, Agent, or Firm*—O'Connell Law Firm

[57] ABSTRACT

A fluorescent imaging system provides an illuminated image of an object that has been subjected to a fluorescent dye, as well as a fluorescence image of the object. Thus, highlighted fluorescent portions of the object are viewed in context with the surrounding environment of the object being viewed. The imaging system includes an optical system which separates illumination light reflected from the object from fluorescence light radiating from the object and provides illuminated and fluorescence images of the object.

20 Claims, 12 Drawing Sheets

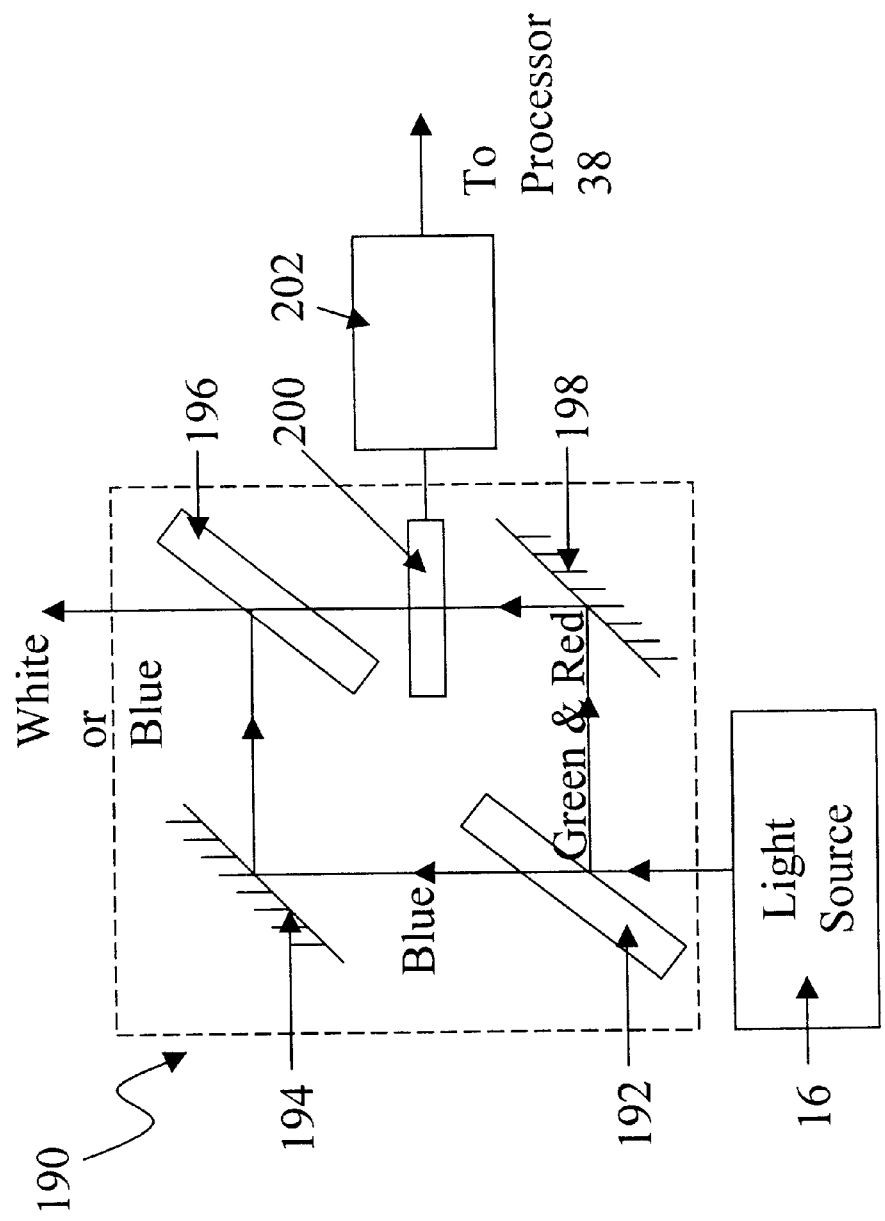

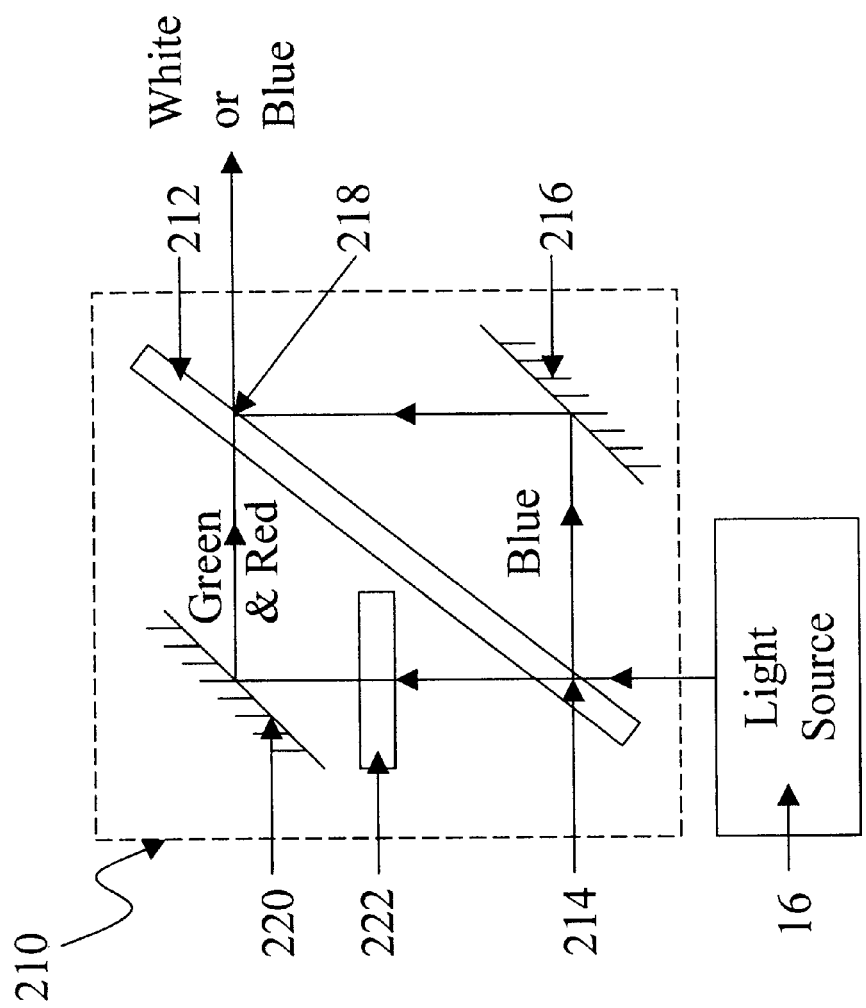

FLUORESCENCE IMAGING SYSTEM

BACKGROUND OF THE INVENTION

This invention relates to the detection of fluorescence and, in particular, the detection of fluorescence for cancer diagnosis.

With conventional endoscopic techniques, early cancer detection presents a diagnostic challenge even for experienced physicians. In its early stages, a cancerous tumor may only be a few cell layers thick, and thus, the surface of the tissue may not physically change sufficiently to be visible when viewed under "white light" illumination with conventional endoscopic techniques. By "white light" illumination, is meant a relatively broad range of the visible portion of the electromagnetic spectrum.

Fluorescence imaging techniques have been used to detect the presence of cancer. Fluorescence is generally defined as the emission of radiation, usually in the form of visible light, resulting from the absorption of radiation in another spectral band from a radiation source. The impetus for using fluorescence imaging in cancer detection was due in part to the recognition that normal and malignant tissue provide different fluorescence features.

One approach for using fluorescence imaging in cancer detection involves comparing the intrinsic fluorescence (also referred to as "autofluorescence" or background fluorescence that is generated by all cells due to the natural presence of fluorescent molecules inside them) of normal tissue with the intrinsic fluorescence of malignantly-transformed tissue.

Another approach for fluorescence imaging in cancer detection involves the use of exogenic substances, including fluorescent dyes, which are administered into a patient and accumulate in malignant tissue. Experiments with cultured cells indicate that the primary cause of dye accumulation in malignant tissue is due to the different metabolism rate of normal and cancerous cells. One advantage of this approach is that the fluorescence can be detected at a peak of the dye's fluorescence spectrum.

SUMMARY OF THE INVENTION

The invention features an imaging system which provides an illuminated image of an object that has been subjected to a fluorescent dye, as well as a fluorescence image of the object. Thus, highlighted fluorescent portions of the object are viewed in context with the surrounding environment of the object being viewed. For example, the invention can be used to detect the presence of cancerous tissue which are highlighted by fluorescence with the surrounding unfluoresced anatomy viewed in natural color.

In a general aspect of the invention, the imaging system includes an optical system which separates illumination light reflected from the object from fluorescence light radiating from the object and provides illuminated and fluorescence images of the object.

Embodiments of this aspect of the invention may include one or more of the following features.

The imaging system includes a camera system which receives one or both of the illuminated and fluorescence images of the object. Images viewed without the camera system are viewed directly, for example, with an optical eyepiece.

In one embodiment, the camera system is electronic (as compared with cameras used for still photography) and generates electrical signals representative of the illuminated and fluorescence images. A first and a second image sensor are used to receive the illuminated and fluorescence images, respectively.

The imaging system includes a display (e.g., CRT monitor) for viewing the illuminated and fluorescence images of the object. The display provides a superimposed view of the illuminated and fluorescence images of the object. Alternatively, the display is divided into regions, each of which is used to view a respective one of the illuminated and fluorescence images, for example, side by side.

A processor receives and processes the electrical signals representative of at least one of the illuminated and fluorescence images of the object from the camera system and generates video signals for the display.

The optical system separates the fluorescence light into a first wavelength range including the wavelength of maximum fluorescence of the fluorescent dye and a second wavelength range different from the first wavelength range. A first optical path receives the illumination light reflected from the object, a second optical path receives the fluorescence light radiated from the object in the first wavelength range and a third optical path receives the fluorescence light from the object in the second wavelength range. First and second optical filters are disposed in the second and third optical paths to limit transmission of fluorescence light in the first and second wavelength ranges, respectively.

Because the fluorescence light from the object is separated into two wavelength ranges the contribution of fluorescence associated with the autofluorescence can be minimized. The resulting fluorescent image, therefore, more accurately represents the fluorescence associated with the dye. Thus, a cancer-contrasting fluorescent dye which has accumulated in malignant tissue is highlighted with increased contrast without risk of being "masked" by the background autofluorescence.

The second image sensor described above has a first region which receives the fluorescence light in the first wavelength range and a second region which receives the fluorescence light in the second wavelength range.

In one embodiment, the optical paths are provided by first and second beamsplitters. The first beamsplitter divides the reflected illumination light between the first image sensor and the second beamsplitter. The second beamsplitter divides illumination light received from the first beamsplitter to the first and second optical filters, respectively.

Alternatively, in lieu of beamsplitters and individual optical filters, an electro-optical filter (e.g., a liquid crystal filter) is controlled to pass the reflected illumination light in a first time period, the first wavelength range in a first portion of the second time period, and the second wavelength range in a second portion of the second time period.

A spectral modulator is disposed between the light source and object to illuminate the object with white light and a non-white, spectral component of the white light (e.g., blue light) in an alternating manner. In one embodiment, the spectral modulator includes a rotatable filter wheel having a first region which passes the white light and a second region limiting transmission to the spectral component.

The imaging system may be used to examine body tissue resected or otherwise removed from the body. In this case, the imaging system includes a base for supporting the object under examination and a non-transparent enclosure attached to the base for enclosing the optical system and light source. An X-Y positioner is used to move at least one of the base and/or the optical system with respect to the other. An imaging system with this arrangement allows a surgeon in the operating room to examine the margins of the removed malignant/premalignant tissue to determine whether additional resection is required. The imaging system can also be used in conventional pathology laboratory settings.

In another aspect of the invention, the imaging described above is utilized with a viewing scope for viewing the object under examination. "Viewing scope" as used here is intended to mean any of the wide variety of instruments used to examine body tissue including endoscopes (e.g., arthroscopes, horoscopes, laparoscopes) used to visualize interior portions of the body, as well as other external viewing devices, such as colposcopes.

The viewing scope includes the optical system described above, a light source to illuminate the object, a distal end enclosing a chamber and a lens system, disposed within the chamber, for viewing at least one of the illuminated image and the fluorescence image of the object. In an endoscope embodiment, the viewing scope includes an insertion section elongated along a longitudinal axis between the chamber at the distal end and a proximal end to be manipulated by a user. The optical system is coupled to the proximal end of the insertion section to receive the illuminated image and the fluorescence image from the lens system.

In another aspect of the invention, a spectral modulator includes an input dichroic beamsplitter which receives white light illumination from the light source and separates a selected color component (e.g., "blue" excitation illumination) from the white light illumination, an output dichroic beamsplitter which receives the separated selected color component from the first beamsplitter along a first light transmissive path and the remaining color components of the white light illumination along a second light transmissive path, and a shutter disposed in the second light transmission path and operable to selectively pass the selected color and the remaining color components from passing to the output dichroic beamsplitter. In operation, the shutter is controlled so that in a closed position, only the selected color component is provided by the spectral modulator. On the other hand, the shutter, in its open position, the remaining color components pass to the output dichroic beamsplitter where they are recombined with the selected color component to produce white light from the spectral modulator.

Among other advantages, a spectral modulator of this construction does not have rotating optical parts, unlike those spectral modulators having filter wheels. The spectral modulator also provides near "lossless" spectral beamsplitting.

In another aspect of the invention, a spectral modulator includes a dichroic beamsplitter which is separated into two regions. A first region receives white light illumination from the light source and separates a selected color component from the white light illumination. The second region receives the selected color component along a first light transmissive path and the remaining color components of the white light illumination along a second light transmissive path. A shutter is disposed in the second light transmissive path and operable to selectively pass the remaining color components to the output dichroic beamsplitter.

In addition to the advantages discussed above with respect to the spectral modulator having input and output dichroic beamsplitters, this construction requires only a single dichroic beamsplitter, thereby reducing the number of parts.

In another aspect of the invention, a method of viewing an image of an object subjected to illumination light from a light source and a fluorescent dye, includes separating the illumination light reflected from the object from fluorescence light radiating from the object and providing an illuminated image of the object and a fluorescence image of the object.

Embodiments of this aspect of the invention may include one or more of the following features.

The method includes displaying the illuminated image and the fluorescence image of the object on a monitor. For example, in one embodiment, the illuminated image and the fluorescence image are displayed as superimposed images of the object. Alternatively, the images are displayed on subdivided regions of the display, one next to the other. Electrical signals representative of at least one of the illuminated image and the fluorescence image of the object are generated. The electrical signals representative of the illuminated image and the fluorescence image of the object from the camera system are processed and video signals representative of the object for display are generated.

Other features and advantages will become apparent from the following description and from the claims.

BRIEF DESCRIPTION OF THE DRAWINGS

FIG. 12 is an alternative embodiment of a spectral modulator.

FIG. 13 is another embodiment of a spectral modulator.

DESCRIPTION

Figure 1:
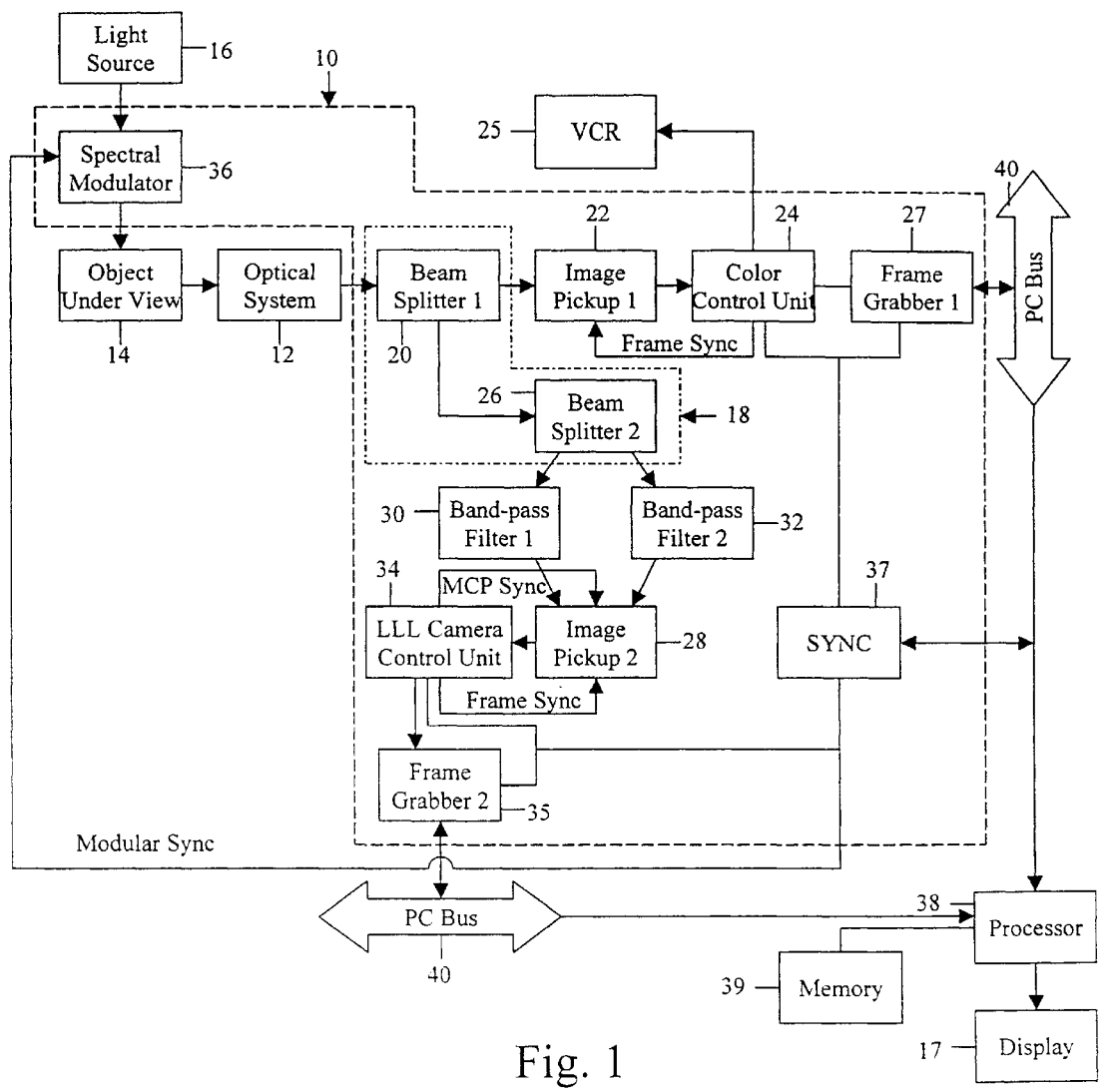
FIG. 1 is a block diagram of a fluorescence imaging system.

Referring to FIG. 1, a fluorescence imaging system 10 (shown surrounded by a dashed line) is used in conjunction with an optical system 12 to view an object 14 that has been subjected to a fluorescent dye (e.g., fluorescein) and is being illuminated by a light source 16. As is described in greater detail below, light source 16 is modulated to alternately illuminate object 14 with "white" light providing normal visualization of the object and fluorescence excitation light (e.g., "blue" light) providing visualization of highlighted fluorescent portions of the object. The fluorescence excitation light is selected to be in a spectral range which provides a high level of fluorescence for the selected dye.

In one embodiment, the fluorescence imaging system 10 superimposes a fluoresced image of object 14 obtained during illumination by blue light over a color image of object 14 during illumination by white light for view on a display 17.

For example, in the field of cancer detection, object 14 is body tissue, such as an organ, being diagnosed for the presence of cancer tissue. The fluorescence imaging system 10 provides a surgeon with a full color image of a the body tissue contrasted with a superimposed fluoresced image of the body tissue indicating areas with cancer. As will be described in greater detail below, optical system 12 may be an endoscope for visualizing the organ within the body.

Fluorescence imaging system 10 includes a spectral modulator 36 (described in greater detail below) and a beam splitter assembly 18 having a first beam splitter 20, such as a beam-splitting cube or mirror. First beam splitter 20 passes a portion of the light from optical system 12 toward a color image pickup device 22 (e.g., a charge-coupled device (CCD)). Image pickup device 22 converts optical images of received light into electrical image signals and provides these signals to a color control unit 24. Color control unit 24 includes circuitry for controlling image pickup device 22 and image processing circuitry which converts the electrical image signals to digital signals for each pixel of image pickup device 22. The digital signals from color control unit 24 are received by a frame grabber 27 which captures the color image of object 14 on a frame-by-frame basis. A video tape recorder 25 may be connected to camera control unit 24 to provide a videotape recording of the examination.

The remaining portion of the light not transmitted to image pickup device 22 is passed to a second beam splitter 26 which provides a pair of laterally separated images onto the photosensitive front surface of a low-level light (LLL) image pickup device 28. The increased sensitivity to light provided by this type of image pickup device is advantageous in detecting the fluoresced image which is generally of much lower intensity than the reflected light received by image pickup device 22. The laterally separated images are passed through respective ones of a pair of bandpass filters 30, 32 before being received by LLL image pickup device 28 which provides images of object 14 in a pair of preselected wavelength ranges. Bandpass filter 30 passes light at a peak wavelength associated with the maximum peak in the fluorescence spectrum of the particular fluorescent dye (e.g., fluorescein) injected or otherwise administered to object 14. Bandpass filter 32 passes light at an optimum wavelength for minimizing the contribution of light intensity associated with the autofluorescence of the object. Bandpass filters 30, 32 have a relatively narrow wavelength band of about 15 nm which is less than approximately one third the spectral width of the fluorescence spectrum of the dye.

Analog electrical image signals representative of the filtered images are generated by image pickup device 22 and are provided to a LLL camera control unit 34 where the image signals are combined and converted to digital signals. The digital signals from LLL control unit 34 are received by a frame grabber 35 which captures the fluoresced image of object 14 on a frame-by-frame basis.

A SYNC circuit 37 provides synchronization signals to color control unit 24, LLL control unit 34, frame grabbers 27, 35 and spectral modulator 36 (e.g., a shuttering mechanism) which, as will be described in greater detail below, is used with light source 16 to alternately illuminate object 14 with white light and fluorescence excitation light (e.g., blue light).

A processor 38 receives data from color camera control unit 24 and LLL control unit 34 via a bus 40 and manipulates the data to superimpose the color and fluoresced images received from camera control unit 24 and LLL control unit 34, respectively, for viewing on display 17.

Figure 2:
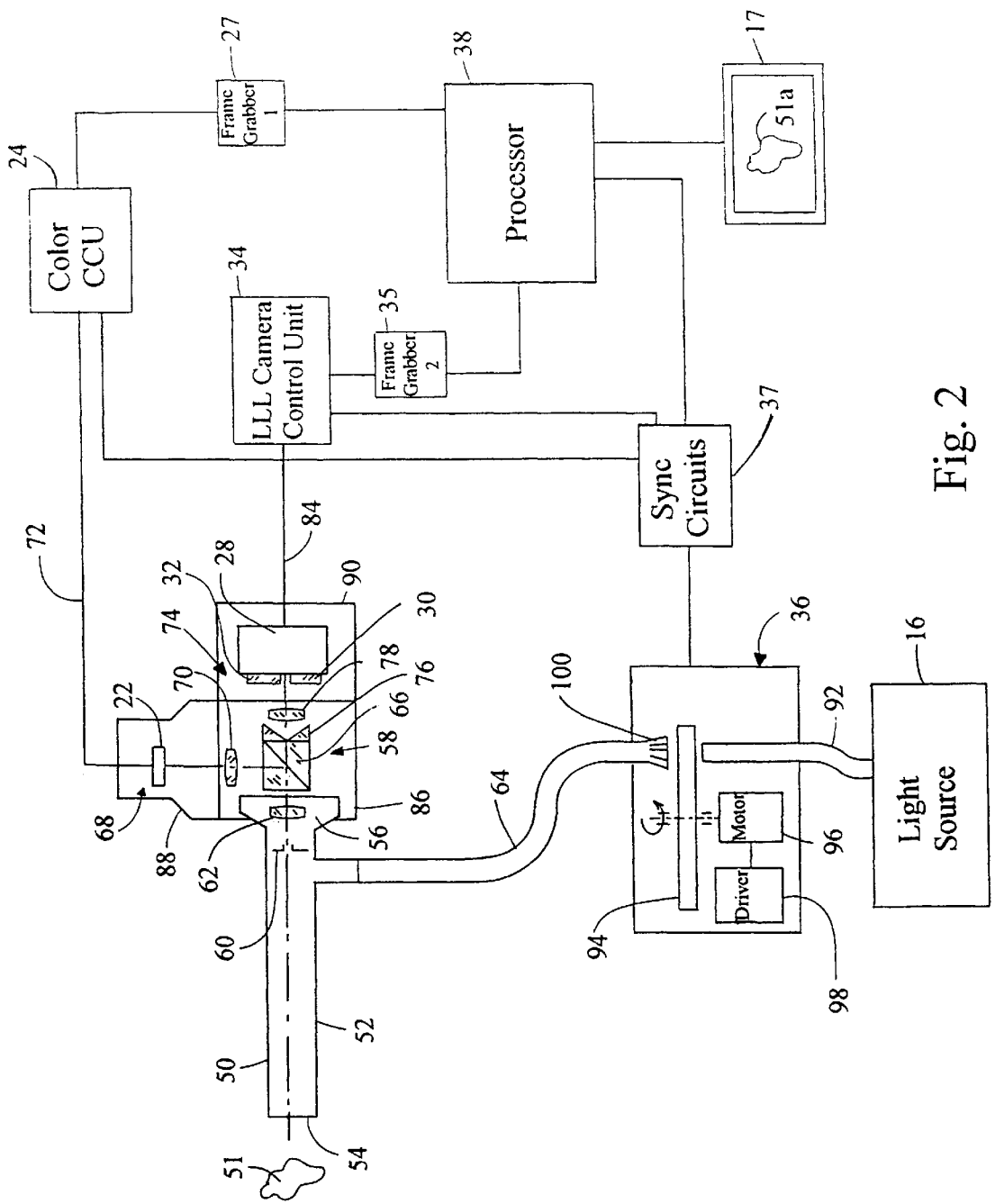
FIG. 2 is a schematic representation, diagrammatic in part, of an endoscope embodiment of the fluorescence imaging system of FIG. 1.

Referring to FIG. 2, in one embodiment of fluorescence imaging system 10, optical system 12 is in the form of an endoscope 50. In one application involving cancer detection, endoscope 50 is used to visualize an organ 51 having a malignant tumor. The organ has been injected or otherwise administered with a non-toxic, cancer-contrasting dye called fluorescein. As will be discussed in detail below, fluorescein is particularly well-suited as a cancer-contrasting dye due to its high fluorescence level, its nontoxicity, and its relatively high retention in cancerous tissue.

Endoscope 50 has an elongated insertion section 52 (rigid or flexible) for insertion into a body cavity or narrow body passage to observe an organ 51 disposed therein. Endoscope 50 may be, for example, a Hysteroscope available from Smith & Nephew, Inc., Part No. 4511. Insertion section 52 extends along a longitudinal axis of endoscope 50 from a distal end 54 to a proximal end 56 where the image of organ 51 is formed in the vicinity of a field stop 60 (or on the rear face of a coherent fiber bundle, in the case of a flexible endoscope). An ocular lens 62 positioned at proximal end 56 of endoscope 50, forms the virtual image of organ 51 at a normal viewing distance from proximal end 56.

Beam splitter assembly 58 includes first beam splitter 20 (FIG. 1) in the form of a splitting cube 66 which reflects a portion of the light from endoscope 50 toward color image pickup device 22 (e.g., a color CCD) of a color camera head 68, such as Part No. 7204956, available from Smith & Nephew, Inc. Beam splitter assembly 58 also includes a coupling lens 70 for focusing the reflected image onto the image plane of color image pickup device 22. As discussed above, image pickup device provides electrical signals representative of the color image of object 14 during illumination by white light. A cable 72 extends from camera head 68 for connection to color control unit 24, for example, Dyonics Digital Camera Control Unit, available from Smith & Nephew, Inc, Part No. 7204562. Color images observed at distal end 54 of endoscope 50 are processed by the color control unit 24 and frame grabber 27 before being transmitted to processor 38 for viewing on display 17 (e.g., a color CRT monitor).

The remaining portion of the light from endoscope 50 passes to LLL image pickup device 28 of a LLL camera head 74. The transmitted portion of this light is further split into a pair of laterally spaced images by second beam splitter 26 (FIG. 1) in the form of a pair of optical wedges 76 laminated to the rear face of splitting cube 66. Optical wedges 76 are desired to be closely positioned with respect to the exit pupil of endoscope 50 to prevent vignetting (i.e., gradual fading at edge regions). Each of the laterally spaced images are passed through respective ones of filters 30, 32 to the photosensitive front surface of LLL image pickup device 28. Beam splitter assembly 58 also includes a lens 78 for focusing the pair of laterally separated images onto the LLL image pickup device 28. Lenses 70 and 78 may be variable focus or zoom type lenses to accommodate endoscopes having field stops of various sizes.

Beam splitter assembly 58 has an outer housing 86 which, in combination with housings 88, 90 of color camera head 68 and LLL camera head 74, respectively, serve as a handle for allowing the user to position elongated insertion section 52 of endoscope 50 appropriately.

Figure 3:
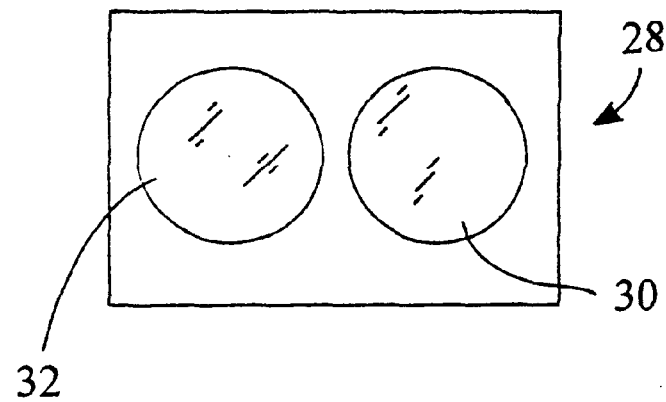
FIG. 3 is a plan view of an image pickup device with laterally separated filter elements used in the embodiment of FIG. 2.

Referring to FIG. 3, optical bandpass filters 30, 32, each selectively pass light from object 14 at relatively narrow ranges of wavelengths. The bandpass filters are produced, for example, using thin-film optical interference technology. In the case where fluorescein is used as the fluorescent dye, bandpass filter 30 passes light in a range between about 508 and 523 nm including a peak wavelength of 516 nm, the wavelength of the maximum peak in the fluorescence spectrum of fluorescein. Bandpass filter 32 passes light in a range between about 489 and 504 nm including wavelength 496 nm, the optimum wavelength for minimizing the contribution of fluorescence caused by autofluorescence, determined using a process described below.

Referring again to FIG. 2, a cable 84 extends from LLL camera head 74 for conveying signals representative of fluorescent images observed at distal end 54 of endoscope 50 to LLL camera control unit 34 and frame grabber 35 where the signals are processed and then transmitted to processor 38 for viewing on display 17.

A light guide cable 64, formed of a bundle of light guiding fiber optic elements, extends from the side of proximal end 56 of endoscope 50 and conveys light, through spectral modulator 36 and from light source 16 to the area of organ 51. In this embodiment, light source 16 may be a Xenon lamp, such as Smith & Nephew, Inc., Part No. 7205353. A suitable light guide cable 64 (Part No. 7205178), is also commercially available from Smith & Nephew, Inc.

Spectral modulator 36 includes a filter wheel 94 driven by a motor 96 and controlled by driver circuitry 98. Light from light source 16 is received by spectral modulator 36, via a relatively short fiber optic cable 92 and is transmitted through filter wheel 94 to light cable 64 through an optical coupler 100.

Figure 4:
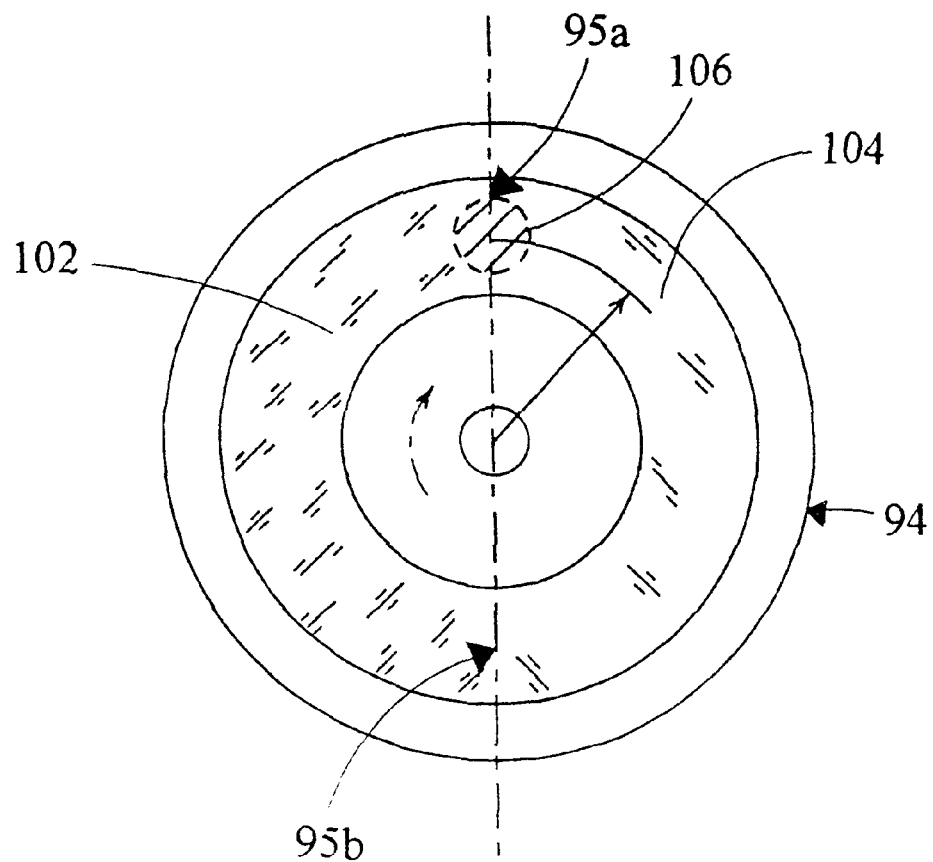
FIG. 4 is a plan view of a rotating filter wheel used in the embodiment of FIG. 2.

Referring to FIG. 4, filter wheel 94 is formed of optical glass and is divided into two equal sized regions 102, 104 (separated along boundary lines 95a and 95b). Excitation filter region 102 passes "blue" excitation light in a spectral range between 400–450 nm. Although visible blue light extends beyond this range, excitation filter region narrows the range of the blue excitation light to avoid possible interference with the fluorescent light emitted by the dye. Clear region 104, on the other hand, allows white light in a relatively broad wavelength range to pass. Although clear region 104 could be an open area, the use of clear optical glass is preferred so that filter wheel 94 is mechanically balanced and compensation is not required.

Filter wheel 94 rotates with the video frequency of display 17 (30 Hz for NTSC standard) and is synchronized with color control unit 24 and LLL camera control unit 34 by SYNC circuit 37. In general, the fluorescent imaging system 10 is synchronized so that during one half of the video period required to scan a video frame of display 17, an image beam 106 incident on filter wheel 94 passes through excitation filter region 102. During this half of the video period, fluorescent images from LLL image pickup device 28 are acquired by LLL camera control unit 34. During the other half of the video period, the image beam incident on filter wheel 94 passes through clear region 104 and LLL image pickup device 28 is turned off so that only color images are acquired by color control unit 24. In other words, LLL image pickup device 28 is electronically turned off when any part of image beam 106 is incident upon clear region 104. Turning off LLL image pickup device 28 during this period protects it from high levels of illumination. On the other hand, color image pickup device 22 may be electronically turned off during "blue" illumination periods or may be left on continuously. In the latter case, the gain associated with the blue color channel for color camera control unit 24 is preferably reduced so that intensity level of blue is consistent with the red and green channels.

The size of filter wheel 94 is dependent in large part on the size of the illuminating beam cross section. Thus, filter wheel 94 is closely positioned with respect to the light emitting face of fiber optic cable 92 so that the image beam is relatively small. In certain applications, optical beam shaping elements may be used to focus light emanating from fiber optic cable onto filter wheel 94. Filter wheel 94 is also sized so that the video frame vertical blanking period (approximately 1.2 msec for NTSC standard) coincides with (or slightly exceeds) the time intervals during which boundary lines 95a, 95b cross image beam 106 (as shown in FIG. 4).

The following equation is used to determine the radius of the path on the surface of filter wheel 94 image beam 106 traverses:

$$r = d/(\pi t_{vb} f_v) + a \tag{1}$$

where d is the diameter of light beam 106;

$t_{vb}$ is the vertical blanking period;

$f_v$ is the vertical scanning frequency (60 Hz for NTSC); and a is a correction factor for ensuring that the crossing of image beam 106 with boundary lines 95a, 95b is within the vertical blanking period.

Processor 38 receives and processes the color and fluoresced images received from color control unit 24 and LLL camera control unit 34, respectively, to provide a superimposed real-time image which is viewed on display 17. Each frame of the color image from color control unit 24 is digitized and stored by frame grabber 27. On the other hand, additional processing is required for processing the pair of laterally separated and filtered images which were passed through respective ones of bandpass filters 30, 32. As discussed above, these filtered images represent the intensity of light at a wavelength of maximum fluorescence of the dye and the intensity of light at a wavelength selected for optimal discrimination of the autofluorescence from the object being viewed. Processor 38 processes the digitized fluorescent images on a pixel-by-pixel basis using the following relationship:

$$F = (R_{tis} - I_2/I_1)/(I_2/I_1 - R_{dye}) \tag{2}$$

where

F is the intensity of the pixel;

$I_1$ is the fluorescence intensity at wavelength $\lambda_1$ of the maximum fluorescence of the selected dye;

$I_2$ is the fluorescence intensity at wavelength $\lambda_2$ for optimum autofluorescence discrimination;

$R_{tis}$ is the ratio $I_2/I_1$ for particular tissue being examined without dye; and $R_{dye}$ is the ratio $I_2/I_1$ for the particular dye.

In general, equation (2) generates a calculated value F for each pixel which maximizes the contrast of fluorescence associated with the dye at wavelength $\lambda_1$ by minimizing the contribution of background fluorescence emitted from the tissue. Thus, the surgeon, can be confident that the superimposed fluoresced image being viewed represents fluorescence relating to the dye collected in the tissue.

Bandpass filters 30, 32 ensure that the measurement of $I_1$ and $I_2$ are accurately performed at wavelengths $\lambda_1$ and $\lambda_2$, respectively.

$R_{tis}$ is specific for the particular type of tissue (e.g., stomach, bladder, skin) under examination. Both $R_{tis}$ and $R_{dye}$ are also specific to the measurement characteristics associated with the particular device (e.g., endoscope) used in the examination. Thus, a calibration procedure is typically performed with the device prior to establishing $R_{tis}$ and $R_{dye}$. Because, $R_{tis}$ and $R_{dye}$ can be determined in advance, their values for specific dyes and types of tissue can be stored in look-up tables in a memory 39 (FIG. 1) associated with processor 38.

It is important to note that equation (2) used by processor 38 to determine the fluorescence intensity is dependent solely on measurements at two wavelengths, $\lambda_1$ and $\lambda_2$. It is also an important advantage that the selection of wavelengths for $\lambda_1$ and $\lambda_2$ fluorescence detection depends only on the particular dye and are independent of the type of tissue being examined.

Wavelength $\lambda_1$ of the maximum fluorescence of the selected dye for bandpass filter 30 is determined simply from a spectral analysis of the dye itself.

Figure 5:
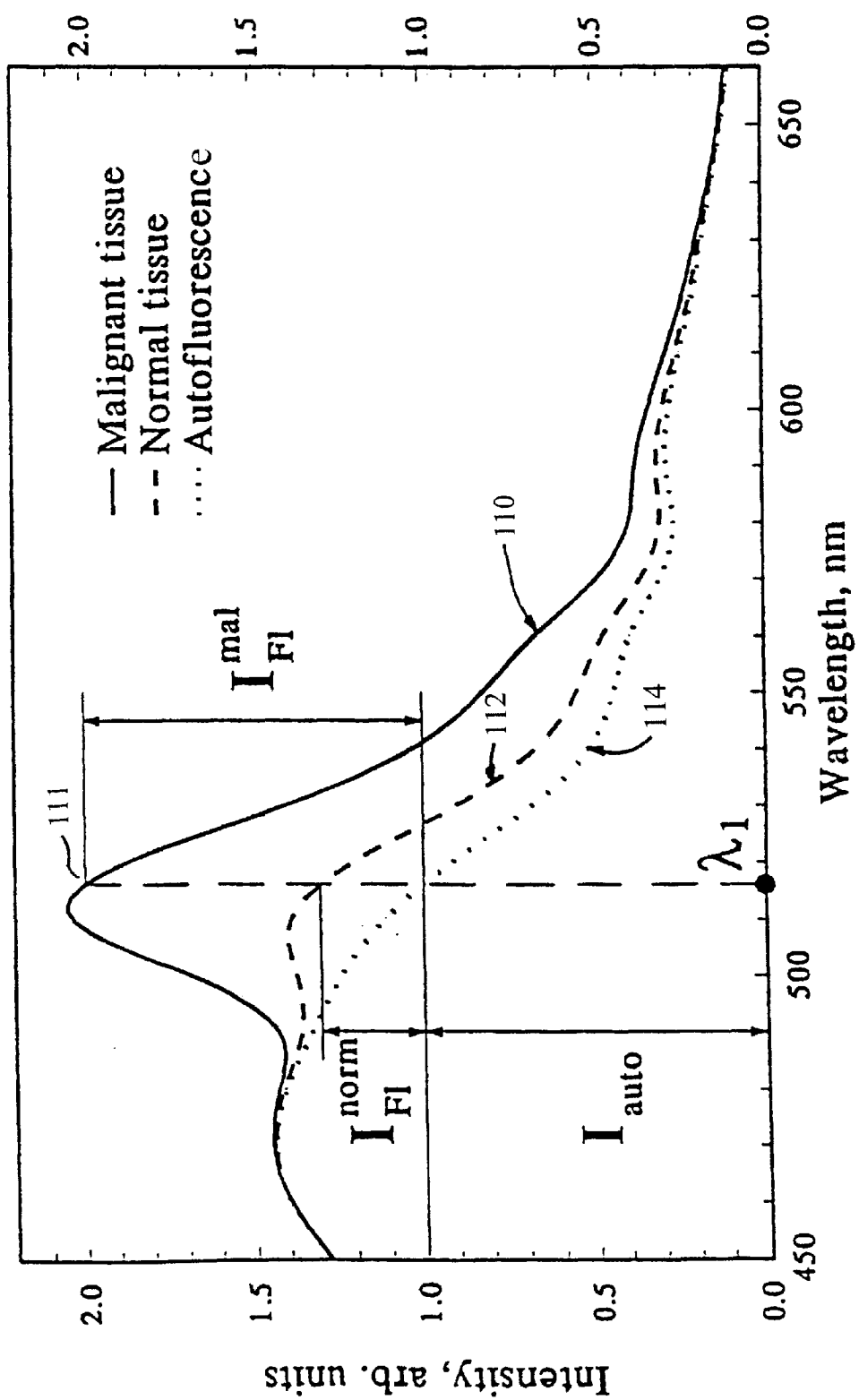
FIG. 5 is a graph depicting intensity of fluorescence as a function of wavelength for normal and malignant tissue administered with fluorescein.
Figure 6:
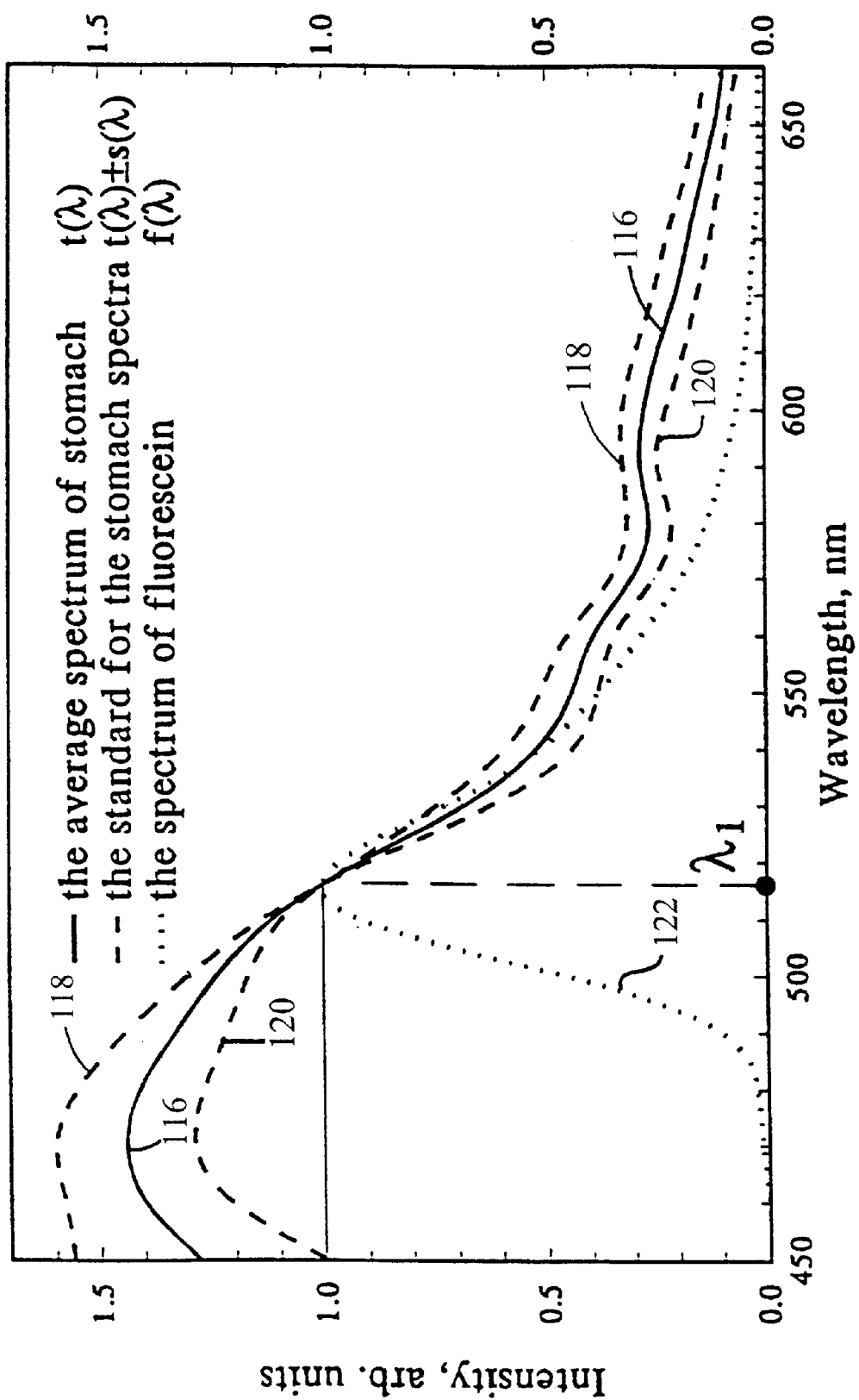
FIG. 6 is a graph depicting intensity of autofluorescence as a function of wavelength for stomach tissue.

With reference to FIGS. 5 and 6, an algebraic approach for obtaining the optimum discrimination wavelength $\lambda_2$ for bandpass filter 32 follows.

Referring to FIG. 5, the intensity spectra is shown for malignant tissue injected with fluorescein (line 110), normal tissue with fluorescein (line 112), and the autofluorescence of the tissue (line 114). Note that the peak of maximum fluorescence for fluorescein at wavelength $\lambda_1$ (516 nm) is not coincident with the peak of the spectrum for the malignant tissue. This is a result of the contribution of autofluorescence to the malignant tissue spectrum.

The value of F calculated using equation (2) is actually representative of the ratio of intensity of fluorescence $I_{F1}$ associated with fluorescein to the intensity of the autofluorescence $I_{auto}$:

$$F = I_{F1}/I_{auto} \qquad (3)$$

As shown in FIG. 5, $I_{F1}$ for malignant tissue is much greater than that of normal tissue. To show that equation (2) is equivalent to equation (3) the total fluorescence intensities for wavelengths $\lambda_1$ and $\lambda_2$ are:

$$I(\lambda_1) = I_1 = I_{f1} + I_{auto} \qquad (4)$$

$$I(\lambda_2) = I_2 = R_{dye} I_{f1} + R_{tis} I_{auto} \qquad (5)$$

The pair of terms in equation (5) correspond to the fluorescence intensities at $\lambda_2$ for the dye and tissue independently. Dividing equation (5) by equation (4) results in the following expression:

$$I_2/I_1 = [R_{dye}(I_{f1}/I_{auto}) + R_{tis}]/[(I_{f1}/I_{auto}) + 1]$$

Substituting F for $I_{f1}/I_{auto}$ and solving for F provides equation (2).

As shown in FIG. 5, the value of F is different for normal and malignant tissues. In accordance with equation (3), it is directly proportional to the concentration of dye present in the tissue under observation.

The exact value of $R_{tis}$ cannot be determined during fluorescence imaging or in advance because the value for different types of tissue as well as samples of each particular type of tissue vary. However, a value of $R_{tis}$ for the particular type of tissue can be determined using statistical techniques. In particular, the average value and the scatter (i.e., the statistical variation) of $R_{tis}$ for the same type of tissue may be measured. The dependencies of both of these parameters on wavelength are determined by statistical processing of autofluorescence spectra, normalized to the intensity at wavelength $\lambda_1$.

Referring to FIG. 6, an average normalized spectrum, $t(\lambda) = R_{tis}(\lambda)$ of the autofluorescence (line 116) is provided based on measurements of various samples of stomach tissue shown. The average spectrum plus and minus one standard deviation of the measurement of autofluorescence across the wavelength of interest (i.e., $t(\lambda)+s(\lambda)$ and $t(\lambda)-s(\lambda)$) are represented by line 118 and line 120, respectively. Lines 118 and 120 represent the scatter of $R_{tis}(\lambda)$. Line 122 represents the normalized intensity spectra for fluorescein solution $f(\lambda)$ that is the same as $R_{dye}(\lambda)$.

Using the standard deviation s of $R_{tis}$, the value of F is determined from equation (2) with the standard error:

$$(1+F)(s/(R_{tis} - R_{dye}))$$

Thus, the optimum wavelength $\lambda_2$ for detection of dye can be determined by minimizing an error factor $x(\lambda)$ which is expressed as follows:

$$X(\lambda) = s(\lambda)/(R_{tis}(\lambda) - R_{dye}(\lambda)) = s(\lambda)/(t(\lambda) - f(\lambda)) \qquad (6)$$

$$X'(\lambda_2) = 0 \qquad (7)$$

As shown in FIG. 6, functions $s(\lambda)$ and $t(\lambda)$ are sufficiently smooth (i.e., have no sharp discontinuities) to allow $s(\lambda)$ and $t(\lambda)$ to expressed about point $\lambda_1$ as:

$$s(\lambda) = s'(\lambda_1)(\lambda - \lambda_1);$$

$$t(\lambda) = 1 + t'(\lambda_1)(\lambda - \lambda_1)$$

where $s'(\lambda_1)$ and $t'(\lambda_1)$ are the derivatives of $s(\lambda)$ and $t(\lambda)$. Substituting these expressions into equation (7), the minimum value for $X(\lambda)$ is determined to be at a wavelength $\lambda_2$ for which the following equation is true:

$$1 - f(\lambda_2) = f'(\lambda_2)(\lambda_1 - \lambda_2). \qquad (8)$$

From equation (8) it can be seen that the optimal discrimination wavelength $\lambda_2$ depends only on the dye spectrum $f(\lambda)$ and is independent of $s'(\lambda_1)$ and $t'(\lambda_1)$ which may vary for different dye-containing tissue.

Figure 7:
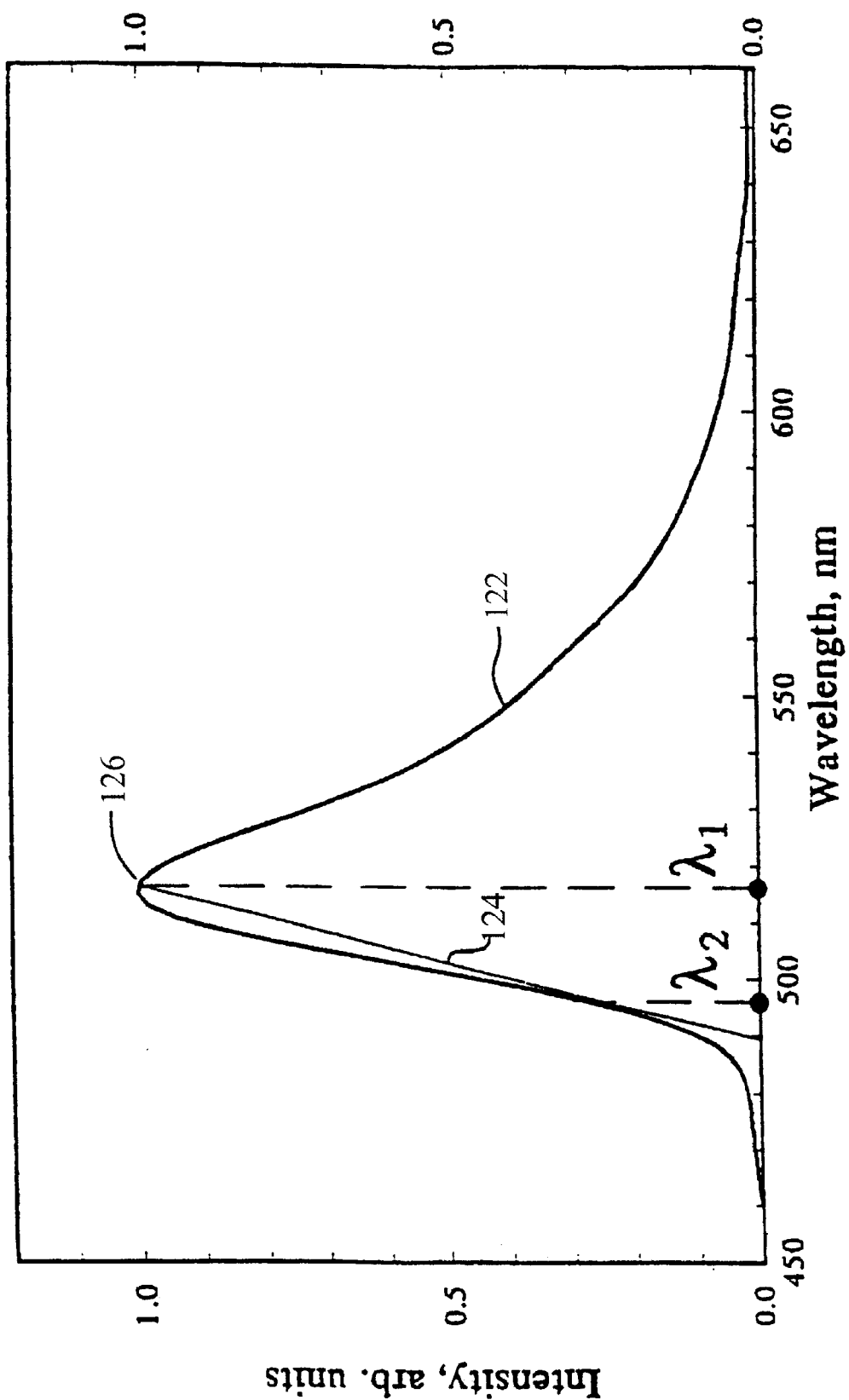
FIG. 7 is a graph depicting a graphical approach for determining the wavelength selected for optimal detection of fluorescein in a background of autofluorescence.

Referring to FIG. 7, a graphical representation of the solution to equation (8) provides an approach for determining wavelength $\lambda_2$. The graphical solution can be performed geometrically by starting at the wavelength of maximum fluorescence $\lambda_1$ for fluorescein dye, which is at the peak (point 126) of spectrum curve 122. A line 124 is then drawn tangent to the spectrum curve and through point 126. The point of tangency provides the optimum value for $\lambda_2$ which for fluorescein is 496 nm.

Figure 8:
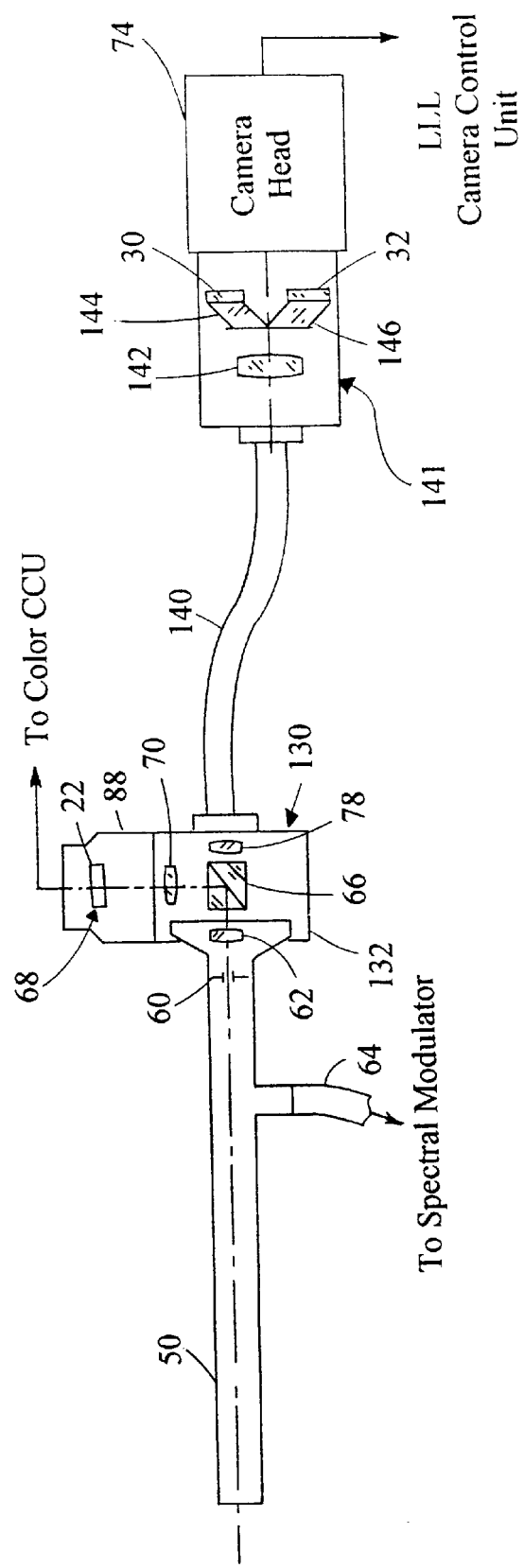
FIG. 8 is an another endoscope embodiment of the fluorescence imaging system.

Other embodiments are within the claims. For example, referring to FIG. 8, a handle 130 for manipulating endoscope 50 is of reduced size. This reduction in size in accomplished by separating first beam splitter assembly 20 from second beam splitter 26. In this embodiment, the beam-splitting arrangement is different from that described above in conjunction with FIG. 2. In particular, splitting cube 66 remains in a housing 132 while second beam splitter 26, enclosed within a housing 141, includes a single lens 142 for projecting the image from the proximal face of fiber bundle 140 onto a pair of rhomboidal prisms 144, 146 having laminated on their rear faces, bandpass filters 30, 32, respectively.

Second beam splitter 26 is optically coupled to beam splitter assembly 20 with a coherent fiber bundle 140. With this arrangement, LLL camera control unit 34 and second beamsplitter assembly 26 can be remotely located from endoscope 50, for example, on a surgical cart.

Figure 9:
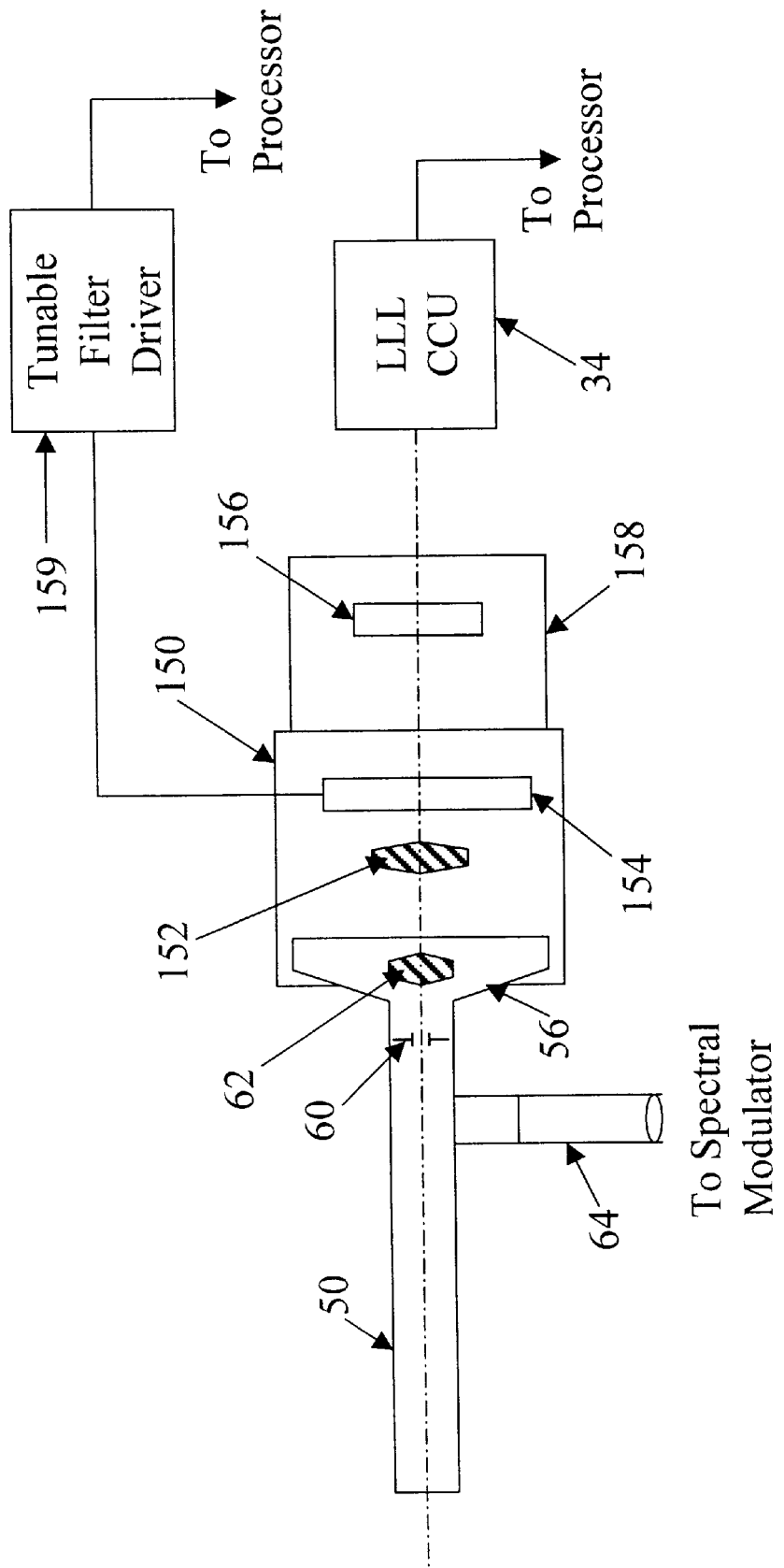
FIG. 9 is still another endoscope embodiment of the fluorescence imaging system.

Referring to FIG. 9, a temporal approach for separating the color and fluoresced images is used rather than the optical beam-splitting approaches described above in conjunction with FIGS. 1 and 8. In this embodiment, a tunable filter assembly 150 having a lens relay system 152 and tunable filter 154 is connected to the proximal end 56 of endoscope 50. The light transmitted through tunable filter 154 is received by a LLL image pickup 156 of a LLL camera head 158. Tunable filter 154 is controlled by a filter driver 159 to divide each image frame into the required full color and fluorescence image acquisition periods. During the full color acquisition period, tunable filter 154 is controlled to pass white light (including red, green and blue (RGB) components images to provide the full color image. During the fluorescence image acquisition period, tunable filter 154 is controlled to pass images at $\lambda_1$ and $\lambda_2$ within the blue portion of spectrum.

The system of this embodiment is synchronized so that LLL camera head 158 is switched by processor 38 (FIG. 1) to a low gain mode during the full color acquisition period and to high gain mode during the fluorescence image acquisition period. Alternatively, the relative time periods for full color and fluorescence image acquisition can be varied. The acquisition time periods may be varied on the basis of the intensity of light available from light source 16 and/or the light efficiency of endoscope 50. For example, when light intensity is high, only one third of the video frame time may be allocated for full color (RGB) acquisition and correspondingly, two thirds for fluorescence. For low light intensities this relationship could be reversed. The timing allocations can be set automatically by processor 38 during calibration or adjusted by the user.

Image acquisition periods for specific wavelength ranges within the full color and fluorescence image periods can also be varied. For example, the time periods for obtaining red, green and blue light can be varied to correspond to the levels of human eye sensitivity to the red, green and blue spectral bands. Generally, the time period for obtaining green light would be longest and shortest for blue light.

A wide variety of image sensors are applicable for use in LLL camera head 158 including Intensified CCD (ICCD), back-illuminated CCD (BCCD), electron-bombarded back-illuminated CCD (EBCCD). However, in the embodiment of FIG. 9, BCCD or EBCCD image sensors are particularly advantageous, since the same image sensor is used to acquire both the full color and fluorescence images. A BCCD image sensor is advantageous because high voltages are not required, but is not recommended where a low power light source is used or the endoscope is too small to yield enough radiation energy.

Tunable filter 154 may be electromechanical (e.g., a filter wheel) or be based on electro-optical principles (e.g., a liquid crystal). Tunable liquid crystal filters are advantageous because they do not require moving parts and are of small size. Ferroelectric liquid crystal tunable filters are particularly advantageous in applications requiring fast switching speeds (in the order of microseconds) allowing the fluorescent imaging system to perform in real time.

Figure 10:
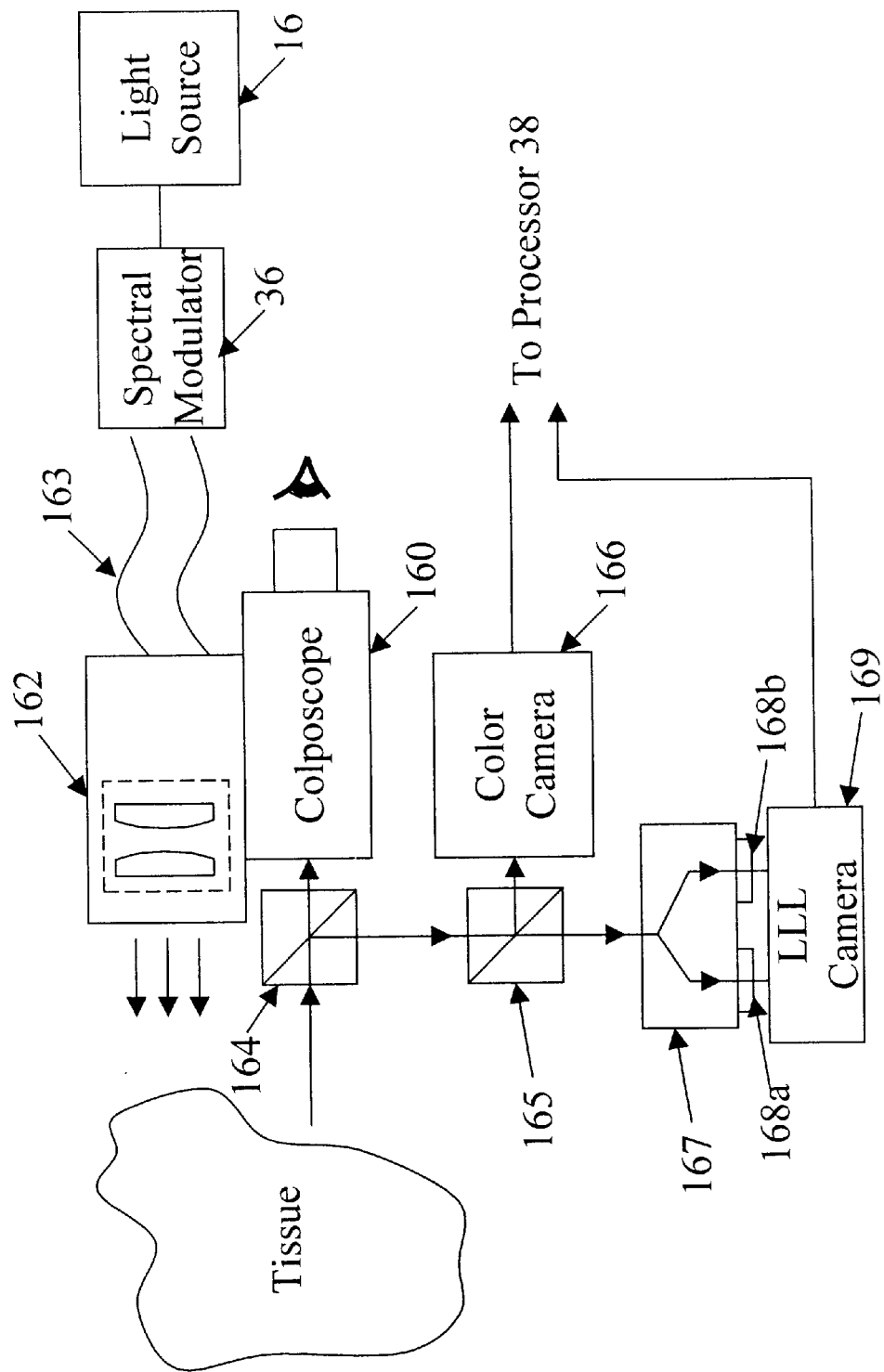
FIG. 10 is an embodiment of the fluorescence imaging system used in conjunction with a colposcope.

Referring to FIG. 10, fluorescent imaging system 10 is used with a colposcope 160 for gynecological examination including examining cervical or vaginal tissue 161. Tissue 161 is illuminated by an illuminator 162 which receives light via a fiber optic cable 163 from light source 16 and spectral modulator 36. Spectral modulator 36 provides blue and full color (white light) in the alternating manner described above. Reflected light from tissue 161 received by a first beamsplitter 164 is divided into two paths, a first portion passed directly to the binocular viewing device of colposcope 160 with the remaining light reflected to a second beamsplitter 165. A yellow filter may be placed in the optical path between first beamsplitter 164 and the viewer to offset overly blue light caused by spectral modulation of the light source. Beamsplitter 164 may also be included within colposcope 160. The light received by second beamsplitter 165 is divided between a color camera head 166 and a third beamsplitter 167 similar to the LLL beamsplitting device described in conjunction with the embodiment of FIG. 8. Third beamsplitter 167 includes bandpass filters 168a, 168b which pass light at wavelengths associated with the fluorescent dye ($\lambda_1$) and with optimum autofluorescence elimination ($\lambda_2$), respectively. The filtered images are received by a LLL camera head 169 and, along with the full color image from color camera head 166, are further processed by processor 38 in the manner described above.

Figure 11:
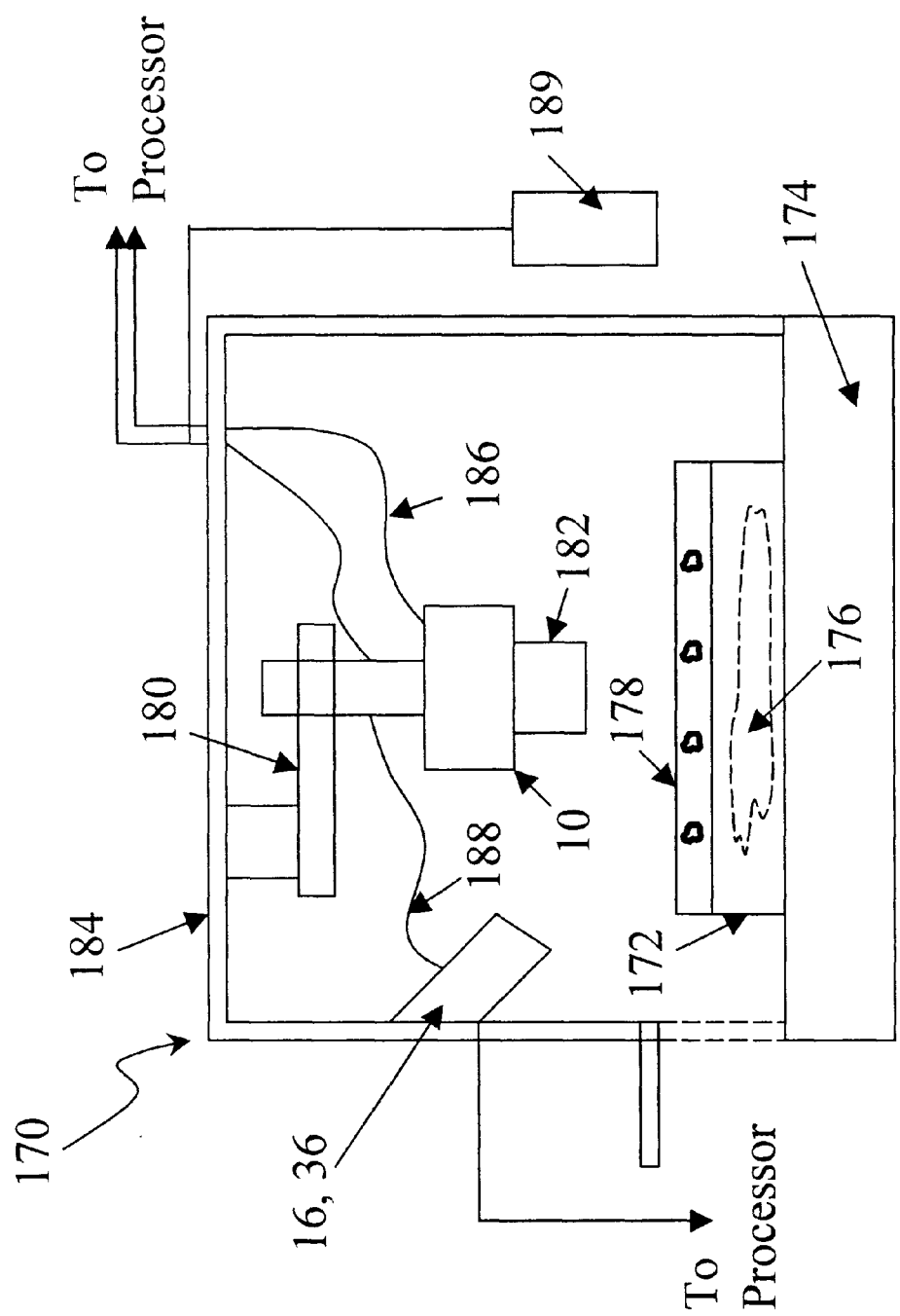
FIG. 11 is an embodiment of the fluorescence imaging system enclosed within a chamber.

Any of the fluorescent imaging systems described above in conjunction with FIGS. 2, 8 and 9 may be adapted for use in analyzing tissue removed from the body. For example, referring to FIG. 11, a system 170 includes a tray or substrate 172 supported on a base 174. The object, such as resected tissue 176 (shown in phantom), is placed on the substrate 172 and covered by a protective glass plate 178. The components of fluorescent imaging system 10 (shown enclosed within dashed lines of FIG. 1) are mounted to an X-Y positioner 180 above substrate 172 and resected tissue 176. Alternatively, fluorescent imaging system 10 may be stationary with substrate 172 mounted to the X-Y positioner.

An optical assembly 182 provides a focused image of the resected tissue to fluorescent imaging system 10. System 170 is enclosed within a non-transparent housing 184 which with base 174 provides an examination chamber to prevent illumination of the resected tissue with ambient room light. Light source 16 and spectral modulator 36 are positioned within housing 10. A remote control box 188 and processor 38 (FIG. 1) are connected by cables 186, 188 to fluorescent imaging system 10, X-Y positioner 180, optical assembly 182, light source 16 and spectral modulator and provide appropriate control, power and synchronization signals therebetween.

System 170 is particularly well-suited for examining the margins of resected malignant/premalignant tissue to determine whether additional resection is required. System 170 may be used in the operating room as well as in conventional pathology laboratory settings. Because system 170 is not manipulated within the body, the small size requirements and real-time performance are not always necessary. Indeed, in certain applications, the video cameras described above may be replaced with still cameras.

Referring to FIG. 12, an alternative embodiment of a spectral modulator 190 includes a first dichroic beamsplitter 192 which receives and divides incoming white light into two components. The first component is a blue component in the wavelength range between about 400–450 nm to a first mirror 194 where it is reflected toward a second dichroic beamsplitter 196. The second component includes red and green components which are reflected by transmitted towards a second mirror 198 where it is reflected by first dichroic beamsplitter 192 toward second dichroic beamsplitter 194. Second dichroic beamsplitter 196 has a construction which is different than that of first dichroic beamsplitter 192 and functions to reflect the blue component and pass red and green components. An "on-off" shutter 200, positioned between second dichroic beamsplitter 194 and second mirror 198, is controlled and synchronized by processor 38 via a shutter driver 202. The construction of the shutter 200 may be based on electromechanical or electro-optical principles. Shutter driver 202 is synchronized so as to keep the shutter 200 open during full color image acquisition and closed during fluorescence image acquisition.

In operation, when shutter 200 is closed, spectral modulator 190 transmits only blue light for fluorescence excitation. On the other hand, when shutter 200 is open, the green and red light reflected from second mirror 198 is recombined with the blue light from first mirror 194 at first dichroic beamsplitter 192 to reproduce the white light. Spectral modulator 190 provides near "lossless" spectral beamsplitting and an arrangement without rotating optical elements.

Referring to FIG. 13, a spectral modulator 210 requiring even fewer optical elements than spectral modulator 190 of FIG. 12 is shown. Spectral modulator 210 includes a dichroic beamsplitter 212 having a first portion 214 which receives white light from light source 16 and reflects blue light toward a first mirror 216 where it is reflected toward a second portion 218 of dichroic beamsplitter 212. The remaining red and green light incident on first portion 214 passes through dichroic beamsplitter 212 where it is reflected by a second mirror 220 toward second portion 218. A shutter 222 is positioned between second portion 218 and second mirror 220 and is controlled and synchronized by processor 38 (FIG. 1) to keep shutter 222 open during full color image acquisition and closed during fluorescence image acquisition. Thus, as was the case in the embodiment of FIG. 12, when shutter 222 is closed, spectral modulator 210 transmits only blue light for fluorescence excitation and when shutter 222 is open, the green and red light reflected from second mirror 220 is recombined with the blue light from first mirror 216 at second portion 218 to produce the white light. Spectral modulator 210 advantageously provides better quenching of residual green and red components in the blue light than that provided by spectral modulator 190 because the blue light is reflected twice by dichroic beamsplitter 212.

The use of fluorescein as a cancer-contrasting dye was used in the descriptions of the above embodiments. However, the imaging systems described above can use other dyes including hematoporphyrin and its derivatives. The approach described above for improving the contrast of a fluorescent image by minimizing the contribution of fluorescence due to autofluorescence is equally applicable to fluorescent dyes other than fluorescein.

Still other embodiments are within the scope of the claims.

What is claimed is:

1. An imaging system for viewing an image of an object under examination wherein the object is subjected to a fluorescent dye and light from a light source, the imaging system comprising an optical system comprising:

a light source for illuminating an object with light to generate an image wherein the light source comprises a means for illuminating an object with white light to generate a full color image of the object and a means for illuminating an object with a spectral component of white light to generate fluorescence images of the object;

a first optical path for receiving the full color image of the object;

a second optical path for receiving a fluorescence image of the object in a first wavelength range $\lambda_1$;

a third optical path for receiving a fluorescence image of the object in a second wavelength range $\lambda_2$ different from the first wavelength range $\lambda_1$ whereby there are two fluorescence images;

a means disposed in the second optical path for limiting transmission of fluorescence light in the first wavelength range $\lambda_1$;

a means disposed in the third optical path for limiting transmission of fluorescence light in the second wavelength range $\lambda_2$;

wherein $\lambda_1$ is a peak wavelength in a fluorescence spectrum of the fluorescent dye and $\lambda_2$ is determined from a normalized fluorescence spectrum $f(\lambda)$ of the fluorescent dye in accordance with the equation $1-f(\lambda_2)=f(\lambda_2)(\lambda_1-\lambda_2)$; and a means for generating a resulting fluorescence image by processing the fluorescence image of the object in the first wavelength range $\lambda_1$ and the fluorescence image of the object in the second wavelength range $\lambda_2$.

2. The imaging system of claim 1 further comprising a display for viewing the full color image and the resulting fluorescence image of the object.

3. The imaging system of claim 2 further comprising a means for generating on the display a superimposed view of the full color image and the resulting fluorescence image of the object.

4. The imaging system of claim 2 wherein the display is divided into first and second display regions, the first region for viewing the full color image and the second region for viewing the resulting fluorescence image of the object.

5. The imaging system of claim 2 further comprising a base for supporting the object under examination and a non-transparent enclosure attached to the base for enclosing the optical system and light source.

6. The imaging system of claim 5 further comprising an X-Y positioner for moving at least one of the base and optical system with respect to the other.

7. The imaging system of claim 1 wherein the means disposed in the second optical path for limiting transmission of fluorescence light in the first wavelength range $\lambda_1$ comprises a first optical filter and wherein the means disposed in the third optical path for limiting transmission of fluorescence light in the second wavelength range $\lambda_2$ comprises a second optical filter.

8. The imaging system of claim 7 further comprising a camera system with a means for generating electrical signals representative of the full color image and the fluorescence images wherein the camera system includes a first image sensor for receiving the full color image and a second image sensor for receiving the fluorescence images.

9. The imaging system of claim 8 wherein the second image sensor has a first region for receiving the fluorescence image in the first wavelength range $\lambda_1$ and a second region for receiving the fluorescence image in the second wavelength range $\lambda_2$.

10. The imaging system of claim 9 further comprising a first beamsplitter and a second beamsplitter, wherein:

the first beamsplitter divides the light reflected and radiated from the object between the first image sensor and the second beamsplitter to allow the first image sensor to receive the reflected full color image; and the second beamsplitter divides the light received from the first beamsplitter between the first and second optical filters, respectively, to allow the second image sensor to receive the fluorescence images.

11. The imaging system of claim 1 wherein the means disposed in the second optical path for limiting transmission of fluorescence light in the first wavelength range $\lambda_1$ and the means disposed in the third optical path for limiting transmission of fluorescence light in the second wavelength range $\lambda_2$ comprise an electro-optical filter controlled to pass the reflected full color image in a first time period, the fluorescence image of the first wavelength range $\lambda_1$ in a second time period, and the fluorescence image of the second wavelength range $\lambda_2$ in a third time period.

12. The imaging system of claim 11 wherein the electro-optical filter is a tunable liquid crystal filter.

13. The imaging system of claim 1 further comprising a spectral modulator disposed between the light source and an object to be viewed for causing the light source to alternatingly illuminate the object with white light and a spectral component of white light.

14. The imaging system of claim 13 wherein the spectral modulator includes a rotatable filter wheel with a first region that allows white light to pass and a second region limiting light passage to the spectral component of white light.

15. A method of viewing an image of an object under examination wherein the object is subjected to a fluorescent dye and light from a light source, the method comprising the steps of:
   alternatingly illuminating the object with white light and fluorescence excitation light;
   separating light reflected from the object from fluorescence light radiating from the object;
   receiving a full color image of the object;
   further separating fluorescence light radiating from the object into two different spectral components of fluorescence centered around wavelengths $\lambda_1$ and $\lambda_2$ to yield two fluorescence images of the object corresponding to the two different spectral components of fluorescence;
   receiving the two fluorescence images of the object; and
   generating a resulting fluorescence image by processing the two fluorescence images of the object;
   wherein $\lambda_1$ is a peak wavelength in a fluorescence spectrum of the fluorescent dye and $\lambda_2$ is determined from a normalized fluorescence spectrum $f(\lambda)$ of the fluorescent dye in accordance with the equation:

$$1 - f(\lambda_2) = F(\lambda_2)(\lambda_1 - \lambda_2).$$

16. The method of claim 15 further comprising the step of generating video signals representative of the full color image and resulting fluorescence image of the object for display.

17. The method of claim 16 further comprising the step of displaying the full color image and the resulting fluorescence image of the object on a monitor.

18. The method of claim 17 wherein the step of displaying the full color image and the resulting fluorescence image of the object on a monitor includes superimposing the full color image with the resulting fluorescence image of the object.

19. An imaging system for viewing an image of an object under examination wherein the object is subjected to a fluorescent dye and light from a light source, the imaging system comprising an optical system comprising:
   a light source for illuminating an object with light to generate an image wherein the light source comprises a means for illuminating an object with white light to generate a full color image of the object and a means for illuminating an object with a spectral component of white light to generate fluorescence images of the object;
   a first optical path for receiving the full color image of the object;
   a second optical path for receiving a fluorescence image of the object in a first wavelength range;
   a third optical path for receiving a fluorescence image of the object in a second wavelength range different from the first wavelength range whereby there are two fluorescence images; and
   a spectral modulator disposed between the light source and an object to be viewed for causing the light source to alternatingly illuminate the object with white light and a spectral component of white light wherein the spectral modulator comprises an input dichroic beamsplitter that receives white light illumination from the light source and separates a selected color component from the white light illumination, an output dichroic beamsplitter that receives the selected color component along a first light transmissive path and remaining color components of the white light illumination along a second light transmissive path, and a shutter disposed in the second light transmissive path operable to selectively pass the selected color while blocking the remaining color components from passing to the output dichroic beamsplitter.

20. An imaging system for viewing an image of an object under examination wherein the object is subjected to a fluorescent dye and light from a light source, the imaging system comprising an optical system comprising:
   a light source for illuminating an object with light to generate an image wherein the light source comprises a means for illuminating an object with white light to generate a full color image of the object and a means for illuminating an object with a spectral component of white light to generate fluorescence images of the object;
   a first optical path for receiving the full color image of the object;
   a second optical path for receiving a fluorescence image of the object in a first wavelength range;
   a third optical path for receiving a fluorescence image of the object in a second wavelength range different from the first wavelength range whereby there are two fluorescence images; and
   a spectral modulator disposed between the light source and an object to be viewed for causing the light source to alternatingly illuminate the object with white light and a spectral component of white light wherein the spectral modulator comprises a dichroic beamsplitter with a first region that receives white light illumination from the light source and separates a selected color component from the white light illumination, a second region that receives the selected color component along a first light transmissive path and remaining color components of the white light illumination along a second light transmissive path, and a shutter disposed in the second light transmissive path operable to selectively pass the selected color component while blocking the remaining color components from passing to the second region of the dichroic beamsplitter.

* * * * *